United States Patent [19]
Stern et al.

[11] Patent Number: 5,869,053
[45] Date of Patent: Feb. 9, 1999

[54] 5T4 ANTIGEN FROM HUMAN TROPHOBLASTS

[75] Inventors: Peter Stern; Nicholas Hole, both of Liverpool, England

[73] Assignee: Cancer Research Campaign Technology, Ltd., London, United Kingdom

[21] Appl. No.: 108,144

[22] Filed: Aug. 17, 1993

Related U.S. Application Data

[63] Continuation of Ser. No. 571,622, Nov. 2, 1990, abandoned.

[30] Foreign Application Priority Data

May 4, 1988 [GB] United Kingdom .................. 8805240
Sep. 8, 1988 [GB] United Kingdom .................. 8821078

[51] Int. Cl.$^6$ .......................... A61K 39/00; A61K 39/38; C07K 1/00; C07K 14/00
[52] U.S. Cl. ................................ 424/184.1; 424/204.1; 530/350
[58] Field of Search ............................ 424/184.1, 204.1; 530/350

[56] References Cited

U.S. PATENT DOCUMENTS 4,558,035 12/1985 Johnson ...................... 514/8

OTHER PUBLICATIONS

Stern et al., *J. Immunol.* (1986) 137(5):1604–1609.
Johnson et al., *Amer. J. Repro. Immunol.* (1981) 1:246–254.
Rettig et al., *Int. J. Cancer* (1985) 35:469–475.
Hole et al., "Trophoblast–Specific Glycoprotein Defined by Monoclonal Antibody 5T4," British Society for Immunology & British Transplantation Society 1986 Joint Annual Meeting, Nov. 12–14, 1986, abstract 66.
Stern et al., "Molecular Characterisation of Human Teratocarcinoma–Trophoblast Cell Surface Antigens," *J. Repro. Immun.*, Supp:6 (Jun. 1986).
Anderson et al., "Monoclonal antibodies to human trophoblast and sperm antigens: Report of two WHO–sponsored workshops, Jun. 30, 1986—Toronto, Canada," *J. Repro. Immun.*, 10:231–257 (1987).
Hole et al, "A 72 kD trophoblast glycoprotein defined by a monoclonal antibody", *Br. J. Cancer*, 57:239–246 (1988).
Cho et al., "Characterization of three monoclonal antibodies to membrane co–factor protein (MCP) of the complement system and quantification of MCP by radioassay," *Clin. Exp. Immunol.*, 83:257–261 (1991).
Purcell, et al., "The human cell–surface glycoproteins HuLy–m5, membrane co–factor protein (MCP) of the complement system, and trophoblast leucocyte–common (TLX) antigen, are CD46," *Immunology*, 70: 155–161 (1990).

*Primary Examiner*—Lynette F. Smith
*Attorney, Agent, or Firm*—Morrison & Foerster, LLP

[57] ABSTRACT

A new glycoprotein 5T4 has been identified in human trophoblast. The antigen and fragments thereof and, more particularly, antibodies that recognise the antigen or fragments thereof are of value in relation to cancer diagnosis and treatment, particularly for the routine screening of cervical smears.

13 Claims, 2 Drawing Sheets

5T4 ANTIGEN FROM HUMAN TROPHOBLASTS

This application is a continuation of application Ser. No. 07/571,622, filed Nov. 2, 1990, now abandoned.

THIS INVENTION relates to a new antigenic peptide, isolatable from human trophoblast cell membranes, antibodies to the antigenic peptide, methods of producing the antigen and antibody and the use of the antigen and antibody in diagnosis and in the production of vaccines.

Trophoblast demonstrates some functional properties of neoplastic tissue, namely invasiveness of host tissue and escape from immunological surveillance. Several monoclonal antibodies to trophoblast membrane proteins have been described. In terms of cancer research, the rationale behind this approach has been to identify 'oncofetal' antigens present on both trophoblast and neoplastic cells (Johnson, 1984). If such antigens were restricted to neoplastic tissues, then these reagents would be potentially useful in diagnosis, tumour localisation and drug targeting. Of those monoclonal antibodies that do identify trophoblast oncofetal antigens, relatively few have been fully characterised. A variety of monoclonal antibodies have been shown to be reactive with the placental alkaline phosphatase (PLAP), and these have shown the greatest clinical potential (McLaughlin, 1986). The low level of PLAP in normal non-pregnant sera, and restricted tissue distribution has been useful in monitoring some ovarian carcinomas by a serum assay (McDicken et al, 1985) and radio-imaging (Epenetos et al, 1985; Critchley et al, 1986). However, PLAP-reactive monoclonal antibodies are not reactive with all ovarian carcinomas.

We have now found a new antigen, sometimes designated 5T4 antigen, which is isolatable from trophoblast and which is also expressed by some tumour cell lines. Accordingly, the present invention provides a glycoprotein (5T4 antigen) characterised by the following properties:

a. Molecular weight of 72 KDa on SDS-polyacrylamide gel electrophoresis (PAGE) under reduced conditions; 69KDa under non-reducing conditions.

b. Monomeric structure in the plasma membrane as judged by gel filtration and two-dimensional SOS-PAGE-IEF (iso-electric focusing). Approximate iso-electric point=6.9.

c. Removal of N-linked sugars with N-glycanase reveals a 42 KDa core structure.

d. Native glycoprotein is N-terminus blocked and resistant to digestion with V8 protease, pepsin, chymotrypsin or chemical cleavage with 75% formic acid, hydroxylamine or N-chloro-succinimide.

e. High sensitivity amino acid analysis reveals most abundant residues as approximately 10% glutamic acid, 12% serine, 16% glycine, 9% threonine and 15% alanine.

f. The N-linked carbohydrate structures are not susceptible to endo beta-galactosidase digestion.

g. Following removal of the N-linked sugar the core structure is susceptible to Cleveland peptide mapping yielding major characteristic peptides of 16.5, 14.0 and 10 KDa with chymotrypsin digestion and 22, 13.5 and 11 KDa with V8 protease digestion.

h. Boiled and reduced native 5T4 antigen is also susceptible to V8 protease yielding major glycoproteins of 24, 12.5 and 10 KDa by Cleveland mapping.

i. 5T4 antigen purified by reverse phase chromatography shows an unusually high ratio 280:215 nm absorption.

The present invention also provides proteolytic fragments of 5T4 antigen as well as the 42 KDa core and fragments thereof.

The 5T4 glycoprotein of the invention can be isolated and purified from human trophoblast cells by recovering the syncytiotrophoblast glycoproteins from human placenta, subjecting these glycoproteins to purification by either antibody affinity chromatography or a combination of other chromatographic methods and isolating 5T4 antigen as described in more detail below. Alternatively, the glycoprotein can be prepared by synthetic or semi-synthetic techniques, synthetic techniques involving building up the polypeptide core structure by building up the polypeptide chain by conventional peptide synthesis followed by introducing any appropriate glycosylation by chemical or biological methods. Alternatively the 42 KDa polypeptide core can be produced by recombinant DNA techniques, utilising a synthetic or naturally-occurring DNA encoding the 42 KDa polypeptide core. Such DNA will comprise a first DNA sequence encoding the 42 KDa polypeptide core of 5T4 antigen and a second DNA sequence, not normally found in association with the first sequence, but under whose influence, the first sequence can express the 42 KDa core in a suitable host cell. Suitable techniques include incorporating the selected DNA in a plasmid, transforming a suitable host cell with this plasmid and expressing the DNA in the host cell. The glycosylation of the genetically engineered 42 KD apolypeptide core can then follow by appropriate chemical or biological methods.

The present invention includes DNA encoding and capable of expressing the 42 KDa polypeptide core as well as plasmids including it and host cells transformed with such plasmids.

A further aspect of the present invention provides antibodies that recognise the 5T4 glycoprotein, or fragments thereof or the 42 KDa core or fragments thereof. Such antibodies may be monoclonal or polyclonal antibodies. The antibodies may be prepared by conventional techniques. Polyclonal antibodies may be obtained by using the 5T4 glycoprotein of the invention or fragments thereof or the 42 KDa core or fragments thereof as immunogen injected into small or large animals from whose blood the polyclonal antibodies are recovered by conventional methods. Monoclonal antibodies can be prepared utilising the 5T4 glycoprotein of the invention or fragments thereof or the 42 KDa core or fragments thereof as immunogen in a host animal, immortalising antibody producing cells of the host animal and recovering monoclonal antibody from the immortalised cells.

As an alternative to the use of the 5T4 glycoprotein of the invention, or its 42 KDa core or fragments thereof as immunogen in the raising of antibodies, one can also use a natural product including the 5T4 glycoprotein of the invention, isolatable from trophoblast cells. This material is known as syncytiotrophoblast glycoproteins, (StMPM), which can be isolated from human placenta by known methods. The 5T4 glycoprotein of the invention can be isolated from the StMPM by either antibody affinity chromatography or a combination of other chromatographic methods.

One particular monoclonal antibody that we have isolated and tested is one prepared by hybridoma techniques using StMPM wheat germ agglutin (WGA) glycoprotein as immunogen and which has become known as 5T4.

The antigens (5T4 glycoprotein, fragments thereof, the 42 KDa core and fragments thereof) of this invention and antibodies (that recognise antigens of this invention) are useful as diagnostic tools and in the production of vaccines. The purified 5T4 antigen for example allows the production of a family of related antibodies which recognise different epitopes of 5T4 antigen. Specifically, these antibodies are of interest:

i) in the development of contragestional vaccines since the antigen is expressed very early on in pregnancy;

ii) in foetal typing by the detection of foetal cells in the mother's bloodstream;

iii) as an early warning signal in situations of danger or damage to the foetus e.g. pre-eclampsia;

iv) in tumour screening and diagnosis in vitro and/or in vivo—in this respect it may offer significant advantage over antibodies to PLOP since the antigen is not found in pregnancy serum;

v) in routine monitoring of the female population with respect to premalignant conditions known as cervical intraepithelial neoplasia CIN 1, 2 and 3 detected in cervical biopsies. There is a correlation between the localisation and intensity of 5T4 reactivity in the dysplastic epithelium in CIN 2 and 3 preneoplastic lesions. The labelling intensity corresponds to the severity of the dysplasia with invasive carcinomas of the cervix strongly labelled.

Accordingly, the present invention includes compositions comprising the antigen or antibody of the invention together with a carrier or diluent. The exact nature of the carrier or diluent will depend upon the ultimate application of the antigen or antibody and, in the case where the antigen is to be used as a vaccine (or antibody as a passive vaccine) the carrier will be a parenterally acceptable liquid carrier. On the other hand, when the antigen or antibody is to be used for diagnostic purposes, the carrier may be liquid or solid and solid carriers for the antibody also represent a particularly important aspect of the present invention where the antibody is to be used as a means of purifying the naturally-occurring antigen by techniques of affinity chromatography.

The antigens and antibodies, immobilised or not, may be linked with radioisotopes or other revealing labels for localisation and/or therapy or conjugated with anti-tumour reagents for therapy. The antigen and antibody can be derivatised for use in different forms of assay for antigen concentration.

Specifically, the present invention includes a diagnostic test kit containing, as a solid component, an immobilised antigen or antibody of the invention and more specifically can contain, depending upon the specific type of assay to be used, an antigen and an antibody of the invention, one of which bears a revealing label. The antigen of the invention can be used in methods of in vitro or in vivo diagnosis targeting antibody while the antibody of the invention may be similarly used to target antigen. Such methods are of particular use in the diagnosis of various types of cancer, particularly for mass screening of cervical smears.

5T4 antigen has a relatively limited tissue distribution. It appears to be a pan-trophoblast marker which is expressed by all types of trophoblast examined as early as 9 weeks of development. It is specific for this tissue type within the placenta except for the amniotic epithelium which is also antigen positive. On the basis of immunoperoxidase staining of frozen sections from normal tissue, 5T4 antigen is also expressed by certain epithelial cell types. It should be noted that several 'trophoblast-characteristic' antigens, such as PLAP, are in fact found in normal tissues at trace concentrations (Mclaughlin, 1986). Using a solid phase immunoassay to quantitate the expression of 5T4 relative to normal tissue, 5T4 antigen was found in placental plasma membrane in at least a 1000-fold higher concentration than that found in other normal tissues tested. However, this level of sensitivity would not necessarily detect expression in minor subpopulations of cells within a given tissue.

Several antibodies have exhibited a similar pattern of reactivity with normal epithelial tissues, for example HMFG1 and 2 (Taylor-Papadimitriou et al., 1981; Wilkinson et al., 1984), and CA 1, 2 and 3 (Bramwell et al., 1985), but this has not limited their use in immunoscintigraphy (Pateisky et al., 1985) or diagnosis of neoplasia (Warr and Cruickshank, 1987). In this respect, 5T4 is reactive with tumour cell lines of a diverse, but select origin, including those of a developmental nature, such as choriocarcinoma and embryonal carcinoma. The reason for 5T4 antigen expression by cell lines of such apparent diversity of tissue origin is not clear; the normal cell line types tested are all of embryonic origin. The lack of reactivity with tumour cell lines derived from lung, bronchus and lymphoid tissue is consistent with the immunohistology of the normal tissue types. Other antigen positive tumour cell lines may have been derived from an epithelial component of normal tissue or represent reexpression of embryonic antigen on tumour cells. Several trophoblast antigens have been reported to exhibit a pattern of expression by tumour cell types apparently not detected in the normal cell counterpart (McLaughlin et al., 1982). In the study by Rettig et al. (1985), a series of six monoclonal antibodies were generated against choriocarcinoma cells, one of which was reactive with neoplastic, but not normal, kidney cells; the other mAbs did not demonstrate such a selective expression.

Several trophoblast associated antigens have been reported in the literature to be expressed on tumour cell lines. 5T4 antigen does however appear to be novel. On the basis of reactivity in dot-blots and other criteria, we have specifically excluded PLAP and transferrin as the 5T4 antigen. On the basis of molecular weight in reduced gels, we have further excluded transferrin receptor (Trowbridge et al., 1984), Insulin receptor (Ullrich et al., 1985), EGF receptor (Waterfield et al., 1982), HMFG1 and 2 (Burchell et al., 1983), CA (Wiseman et al., 1984), CEA (Krantz et al., 1979), alpha feto-protein (Ruoslahti, 1979) and all of the placental specific proteins reviewed by Bohn et al.(1983). On the basis of molecular weight and cell line reactivity, none of the monoclonal antibodies described by Lipinski et al. (1981), Sunderland et al. (1981), McLaughlin et al. (1982), Loke et al. (1984), Travers and Bodmer (1984), Rettig et al. (1985), Yamashita et al. (1986) or Mueller et al (1986) appear to recognise this antigen.

The 5T4 antigen is carried by glycoprotein molecules of 72 kD on syncytiotrophoblast microvillous plasma membranes but appears on molecules of similar molecular weight from several different cell lines including some choriocarcinomas. The molecules are sialylated and have approximately 30 kD of the apparent molecular weight due to N-linked carbohydrate structures as judged from removal of the latter by N-glycanase endoglycosidase.

5T4 appears to exist on the cell surface as a monomeric protein. Firstly, 5T4 antigen elutes with an apparent molecular weight in gel filtration of 12 kD, an increase consistent with the addition of a detergent shell, and inferring that 5T4 is not associated non-covalently with any other large molecules. Additionally, reduction with 2-mercaptoethanol does not substantially alter the apparent molecular weight of the 5T4 radio immunoprecipitate, as would be the case if it were disulphide bonded to another protein.

The pattern of expression of 5T4 is similar to that of the family of mucin type glycoproteins (Swallow et al., 1987), but with clear differences from those defined by the CA or HMFG series of antigens (Wiseman et al., 1984; Burchell et al., 1983). These latter glycoproteins are defined by several monoclonal antibodies which have been shown to be reactive with a wide range of malignant tumour cells but also reactive with certain specialized normal epithelia.

Various aspects of the present invention will now be illustrated by the experimental data given below.

MATERIALS AND METHODS

Purification of syncytiotrophoblast glycoproteins

StMPM was purified from full term human placentae, obtained within one hour post partum, by the method of Smith et al. (1974). The StMPM pellet was solubilised in 0.5% DOC in tris-buffered saline (TBS, 0.15M NaCl, 25 mM tris, pH 8.0) containing 0.1 mM phenylsulphonylmethyl fluoride (PMSF) and centrifuged at 14,000 g for 10 minutes. The WGA-reactive glycoproteins were then purified by incubation of the supernatant with WGA-Sepharose (5 mg ligand/ml Sepharose) for one hour at room temperature. The beads were washed extensively in TBS/0.5% DOC, and the specifically bound glycoproteins eluted in 5 ml of 0.2M N-acetyl glucosamine (Sigma) in TBS. The eluted fraction was extensively dialysed against 30 mM ammonium bicarbonate (pH 7.9), and lyophilised.

Generation of Monoclonal Antibody

A male BALB/c mouse was immunised by six intraperitoneal injections of WGA-purified StMPM glycoproteins (100–200 µg/injection). Spleen cells were fused with NS1 murine myeloma cells (Kohler and Milstein, 1975), and the cells plated out in 24-well Linbro plates at $7 \times 10^5$ cells/well. After two weeks, wells were assayed for StMPM reactive antibody by immunodotting. Positive clones were picked directly and further subcloned by limiting dilution. The antibody subclass was determined by double radial diffusion using a monoclonal isotype typing kit (Serotec, Bicester, U. K.). Antibody 5T4 was obtained by this technique.

Cell culture

Details of the cell lines described are found in table 3. Standard tissue culture media, alpha Dulbecco's modified Eagles medium (DMEM), DMEM or RPMI supplemented with antibiotics and 10–20% foetal calf serum (Gibco) were used.

Radioactive labelling of membranes and cells

Near confluent cell cultures of AV-3 cells were radiolabeled for 15–18 hours with $^3$H-glucosamine (20 µCi/ml) (Amersham International) in RPMI containing 10% dialysed FCS. Metabolically labeled cells were collected and immunoprecipitated as follows : cells were removed from tissue culture flasks by incubation in 0.1M EGTA-PBS, washed in PBS (Dulbeccos-A) and then solubilized for 30 minutes at 4° C. in 0.5% (v/v) NP40 in tris-buffered saline (TBS, 0.15M NaCl, 25 mM Tris, pH 8.0) containing 0.1 mM PMSF. Non-solubilized cellular components were removed by centrifugation at 14,000 g and the amount of radioactivity incorporated into protein was determined following precipitation with 10% trichloroacetic acid.

Cell surface labelling by the lactoperoxidase-$^{125}$I method together with the techniques of immunoprecipitation and SDS-PAGE were carried out as previously described; high molecular weight standards (Sigma), red blood cell membrane proteins or $^{14}$C-methylated protein mixtures (Amersham International) were used as marker proteins (Thompson et al., 1984; Stern et al., 1984; 1986). Tritiated sodium borohydride labelling of cell surface glycoproteins was carried out as described by Axelsson et al. (1978) .Autoradiography and fluorography were as described in Thompson et al. (1984) using pre-flashed Fuji X-ray film.

Immunoperoxidase and immunofluorescence labelling

Immunoperoxidase staining of frozen tissue sections was carried out by the method of Bulmer and Sunderland (1983). Tissues were obtained as soon as possible post mortem, always within 12 hours, and processed immediately. Indirect immunofluorescence with cell suspensions was as described previously (Thompson et al., 1984). A monoclonal antibody we have isolated, directed against a widely expressed human antigen (mAB 1D2), was used as positive control.

Radiobinding assay of cell surface antigen expression

Cells were harvested with either EGTA-PBS or EGTA/trypsin, washed and resuspended in Earle's buffered saline solution (EBSS) with 0.5% bovine serum albumin and 0.1% sodium azide at $2-10^6$ cells/ml. The suspensions were plated out at 50 µl ($10^5$ cells)/well in microtitre plates. 50 µl mAb/well were added and incubated at room temperature for one hour. The cells were washed and $5 \times 10^5$ CPM of $^{125}$I-labelled (Fab')$_2$ fragments of sheep anti-murine immunoglobulin (Amersham International) added. Following incubation for one hour at room temperature, the cells were washed, harvested, and bound radioactivity determined on a gamma-counter. Assays were carried out in quadruplicate. Results are expressed as a ratio of specifically bound radioactive CPM relative to CPM with negative control antibodies. In some experiments $10^7$ cells were incubated with 1 ml of fixative (Buffered 10% formalin, Bouins' fixative, 0.25% gluteraldehyde, absolute ethanol or PBS control) for 30 minutes at room temperature and washed in EBSS. After incubation in 0.5% BSA in EBSS for 30 minutes, the cells were then processed as described above.

Preparation of crude membrane from normal human tissues

Tissues were obtained at post mortem held within 12 hours of death, and processed immediately. 10–20 g of tissue was finely chopped, rinsed, and homogenised in 10–20 ml of ice-cold phosphate buffered saline containing 5 mM MgCl$_2$ and 0.1 mM PMSF with 20 strokes of a Dounce homogeniser. The homogenate was centrifuged at 10,000 g for 20 minutes, the pellet discarded and the supernatant centrifuged at 100,000 g for 1 hour. This pellet was solubilised in 0.5% (w/v) DOC/TBS containing 0.1 mM PMSF and unsolubilised material pelleted by centrifugation at 14,000 g. The protein concentration of the supernatant was determined by the method of Lowry et al. (1951). Membranes from 12-hour old placentae were prepared identically and acted as positive controls.

Gel filtration 50 mg of StMPM protein was solubilised in 6.5 ml of 1.0% (w/v) DOC/TBS containing 0.1 mM PMSF, centrifuged at 100,000 g for 30 minutes, and the supernatant fractionated over S200 Sephacryl (Pharmacia). Column size was 90×2 cm, running buffer was 0.1% (w/v) NaDOC/TBS containing 0.1 mM PMSF. Flow rate was 17 ml/hour. Fraction size was 3.3 ml. The column was calibrated with the following proteins; Equine ferritin (Sigma), IgG (Kabi), transferrin (Sigma), Bovine serum albumin (Sigma) and ovalbumin (Sigma). Fractions were assayed for 5T4 antigen in ELISA and immunodot.

ELISA and immunodot

Elisa plates (Dynatech) were activated by one hour incubation with 100 µl/well of PBS containing 0.25% gluteraldehyde (BDH), the plates washed with PBS, and 100 ul/well of undiluted or 10-fold diluted fractions from gel filtration bound to the plates by overnight incubation at 4° C. Following washing, the plates were incubated with 1% BSA/TBS as blocking agent. ELISA was then carried out as described (Johnson et al., 1981). Immunodotting on nitrocellulose was carried out using the Bio-Rad Dot-Blot apparatus. Fractions from gel filtration were loaded at 10 ul and 100 ul/dot. NaDOC solubilised plasma membrane protein was loaded in the range of 50 μg-12.5 ng protein/dot. The following antigens were loaded at 1 μg protein/dot; transferrin (Sigma), PLAP (Gift of Dr. P. J. McLaughlin), human placental lactogen (HPL) (Sigma), calmodulin (Sigma), IgG (Miles Ltd.), albumin (Miles Ltd.) and normal human sera. The nitrocellulose sheet was blocked with 3% (w/v) BSA (Sigma) in TBS and processed as described previously (Webb et al., 1985). In both ELISA and immunodot, mAb 1D2 was used as positive control.

Enzymatic digestion

StMPM membranes (approx. 1 mg protein) were treated overnight at 37° C. with either 2 mg trypsin (Boehringer), 2 mg pronase (Boehringer), 0.1 U neuraminidase (Behringwerke) in 300 μl of PBS or 10 units/ml N-glycanase (Genzyme) in buffer containing final concentrations as follows: 0.17% SDS; 0.2M tris-HCl, pH 8.7; 10 mM 1,10-phenanthroline hydrate (in methanol); 1.25% NP-40 (Plummer et al., 1984). The treated membranes were solubilised in DOC/TBS and 5T4 residual antigenicity assayed by dot-blot. 5T4 immunoprecipitates of detergent solubilised $^{125}$I-radiolabelled StMPM were eluted form protein-A-Sepharose with 0.5% SDS in water and incubated overnight at 37° C. with or without 10 units/ml N-glycanase in buffer as above. Digests were subjected to reduced SDS-PAGE and autoradiography.

Large Scale Preparation of 5T4 Antigen

All procedures were carried out at room temperature. All buffers contained 0.1 mM phenyl methyl sulphonyl fluoride (PMSF). The microvillous membranes from one placenta (approx. 1 g weight) were solubilised in 100 ml of 1% nonidet P40 (NP-40) in TBS (20 mM Tris, 150 mM sodium chloride. pH 8.0) for 30 minutes on a multimixer. Unsolubilised material was pelleted at 100,000 g for 30 minutes. This was loaded onto a wheat germ agglutinin (WGA)-agarose column (Pharmacia; 2 mg/ml ligand, 5 ml column) at 1 ml/minute using Pharmacia chromatography package A apparatus. The column was washed with 50 ml of 1% NP-40/TBS and the specifically bound glycoproteins eluted with two column volumes of 0.3M N-acetyl-D-glucosamine in the same buffer. This fraction was loaded onto a mAb 5T4-sepharose affinity column (2 mg/ml ligand, 1 ml column). The IgGl 5T4 mAb was purified by high salt protein A affinity chromatography (loading buffer 1.5M glycine, 3M NaCl, pH 8.9. Elution buffer 100 mM citrate, pH 6.0) and bound to CNBr-activiated Sepharose (Pharmacia). The mAb 5T4 affinity column was washed with 5 column volumes of 1% NP40/TBS and 5 column volumes of TBS. The bound 5T4 glycoprotein was eluted with 8M urea. Fractions were assessed by immunodot (Stern et al, 1986), protein assay (Lowry, Rosebrough, Farr and Randall, 1951) and SDS-PAGE.

The WGA and 5T4 affinity chromatographic steps give a 10,000 fold purification with approximately 70% yield. Minor contaminants visible in silver stained SDS-PAGE are present at least 100-fold lower protein concentration than 5T4 antigen. Further fractionation by either Superose 12 gel filtration or hydrophobic interaction reverse phase chromatography yields 5T4 molecules devoid of contaminants.

RESULTS

The monoclonal antibody 5T4 is a murine IgGl. All work detailed in this study was carried out using subclone 5T4.B8. The preliminary screen by immunodot showed that the antigen recognised was none of the following major proteins associated with the trophoblast; IgG, transferrin, PLAP, HPL, albumin, calmodulin nor was it detectable in serum.

Tissue distribution

Figure 1:
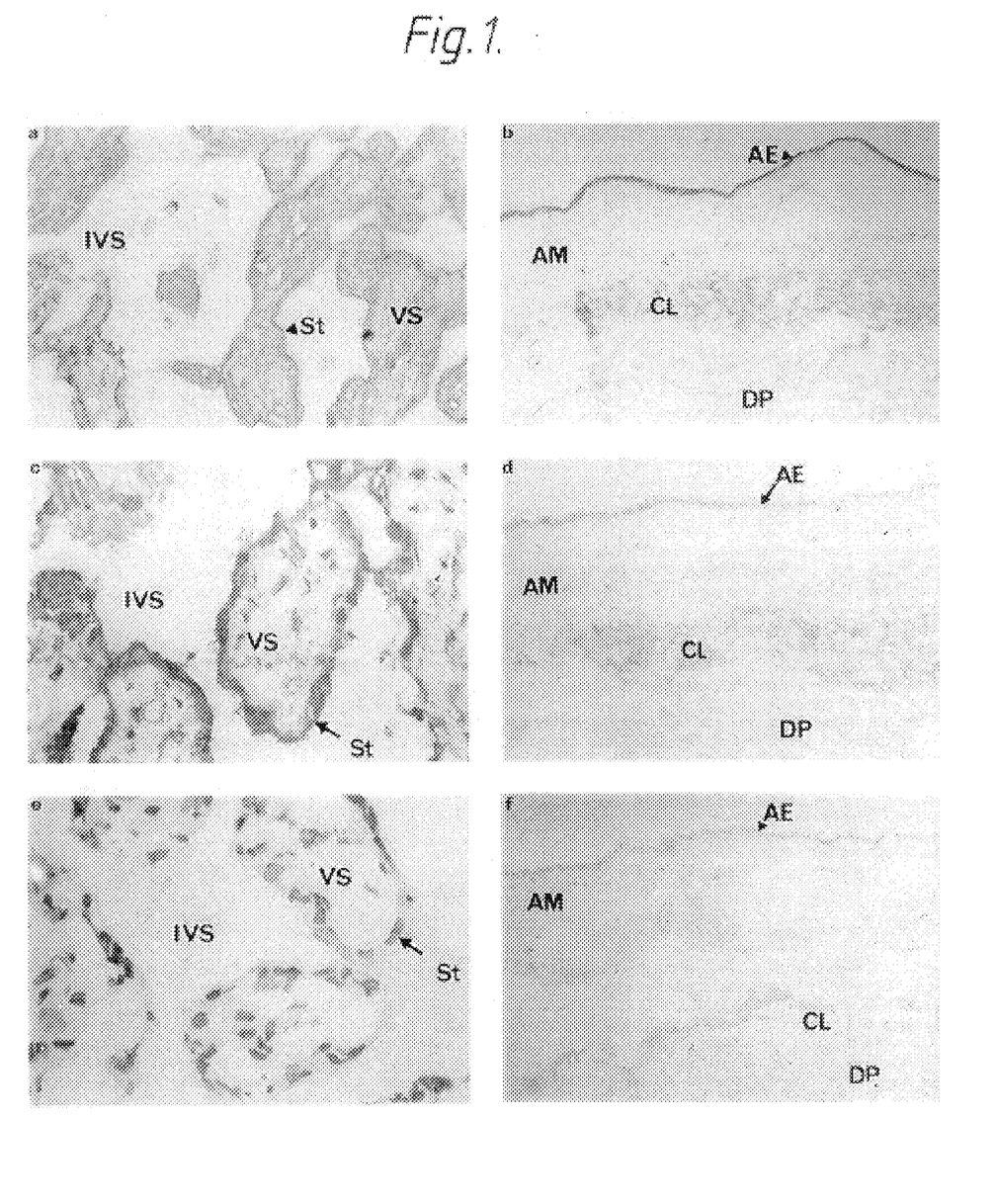

5T4 antigen expression in first trimester and full term placentae was investigated using indirect immunoperoxidase staining of frozen sections. FIG. 1 illustrates antigen expression in term villous placenta as assessed by immunohistology of frozen sections. Villous trophoblast is strongly labelled by mAb 5T4, whereas the stroma is negative. There is specific labelling of the amniotic epithelium and extravillous cytotrophoblast of the chorion laeve but not of the amniotic mesenchyme or maternal decidua (FIG. 1 c,d). Appropriate positive and negative controls are also shown; mAb 1D2 labels all parts of villi (FIG. 1a), mAb H316 labels trophoblast but is not specific for this tissue type (FIG. 1b; Stern et al., 1986); negative controls are unlabelled (FIGS. 1e, f). Extravillous cytotrophoblast in the placental bed is also labelled by mAb 5T4; no other element of the term placenta is 5T4 antigen-positive. Similar analysis of first trimester villous tissue has shown antigen expression by both syncytiotrophoblast and cytotrophoblast (data not shown). The earliest stage examined for 5T4 expression is in a chorionic villous biopsy at 9 weeks gestation which is positive by indirect immunofluorescence (with Dr. Bruce Smith, Jefferson, Philadelphia). This level of analysis suggests that 5T4 antigenic molecules are expressed by representatives of all subpopulations of trophoblastic cells.

5T4 was unreactive with the following non-pregnant tissues examined in immunohistology; spleen, heart, brain, liver, lung, bronchus, skeletal muscle, testis or ovary. Glomeruli in the kidney, villi of the small intestine, bladder epithelium, basal layer of the epidermis, endometrial glands of non-pregnant uterus and endocervical glands showed some specific labelling with mAb 5T4. Some small vessels in various tissues appeared to be weakly stained. Table I summarises 5T4 reactivity assayed by immunohistology of frozen tissue sections.

To further examine 5T4 expression, a semi-quantitative assay of 5T4 antigen on isolated membranes of some of the above tissues was assessed using solubilised proteins in an immunodot assay. 5T4 was still reactive with full term placental plasma membrane protein at an antigen concentration of 50 ng/dot. In contrast to the widely distributed antigen recognised by mAb 1D2, 5T4 was not specifically reactive with any other tissue tested (ovary, testis, kidney, brain, liver and muscle) at all antigen concentrations used (up to 50 μg/dot). From this it was concluded that these normal non-gestational tissues express 5T4 antigen at approximately 1000-fold lower concentration than full-term placenta on a weight of crude membrane protein basis. This relative level of expression is comparable with PLAP as measured using mAb H317 (Table II).

Expression by cell lines

5T4 antigen expression by cell lines of normal and neoplastic derivation was assessed by indirect immunofluorescence and a more quantitative radiobinding assay (Table III). By comparison of reactivity with negative control xenogeneic cell lines, radiobinding indices of greater than 1.5 were considered to indicate positive expression of antigen. Trypsinisation was necessary to remove some attached cell lines from the substratum and it was noted where compared that this procedure tended to reduce the binding index compared with EGTA removal (data not shown). Normal leukocytes were 5T4 antigen negative and "normal" types represented by cell lines of amnion, embryonic lung fibroblasts and embryonic intestine origin were labelled by 5T4 antibodies. Tumour cell lines of myeloid origin were all 5T4 antigen negative; 6/6 tumour cell lines of gestational or developmental origin were positive. 11/15 carcinomas of other histological types and origins were positive, as was one glioma and ⅓ Wilms tumour lines tested.

Immunoprecipitation

Figure 2:
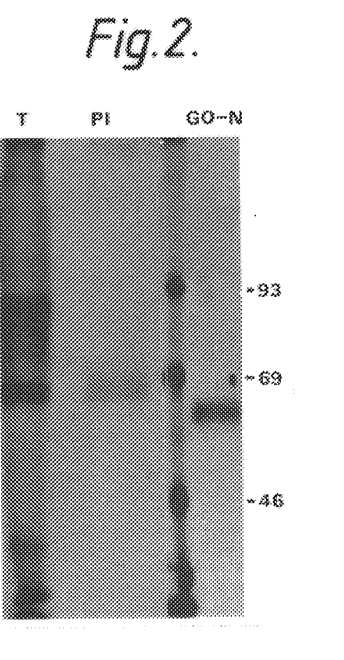

5T4 was unreactive with reduced and unreduced western blots of StMPM. The molecular species bearing the 5T4 antigen was identified as a 72 kD protein by reduced SDS-PAGE analysis of immunoprecipitates from $^{125}$I lactoperoxidase labelled StMPM (FIG. 2, lane 1). The molecules migrate with a molecular weight of 69 kd in unreduced SDS-PAGE. It was observed that the relative mobility in SDS-PAGE varies anomalously with the percentage of the acrylamide. This is sometimes indicative of a glycoprotein, which is confirmed by the change in molecular weight following removal of N-linked sugars by digestion with N-glycanase, yielding a molecule of 42 kd (FIG. 2, lane 2).

Figure 3:
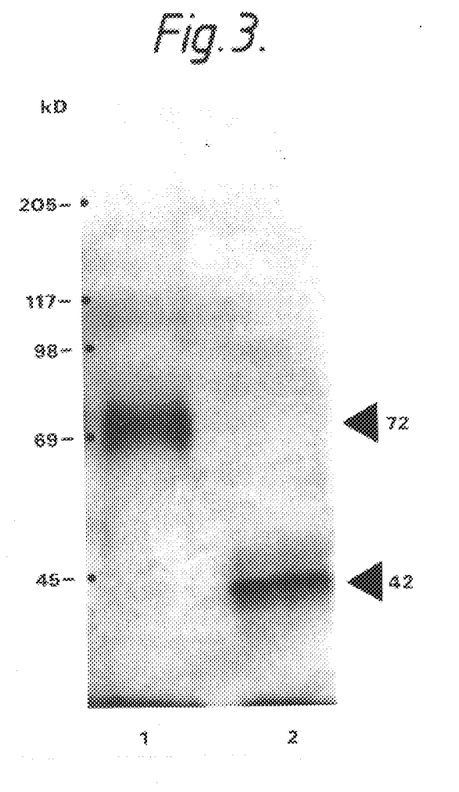

5T4 glycoprotein can be labelled by reduction with tritiated sodium borohydride either after periodate oxidation of sugar residues or galactose oxidase/neuraminidase treatment. These latter treatments change the relative mobility in SDS-PAGE as compared with $^{125}$I labelled 5T4 antigen (FIG. 3). AV-3, Tera-2, MRC-5, Hep-2, HN5, HT29 cell lines all express a molecule of similar molecular weight to that on StMPM as judged by SDS-PAGE of immunoprecipitates of surface iodinated cells; the antigen has been immunoprecipitated from AV-3 cells metabolically labelled with tritiated glucosamine (data not shown).

Gel filtration

Figure 4:
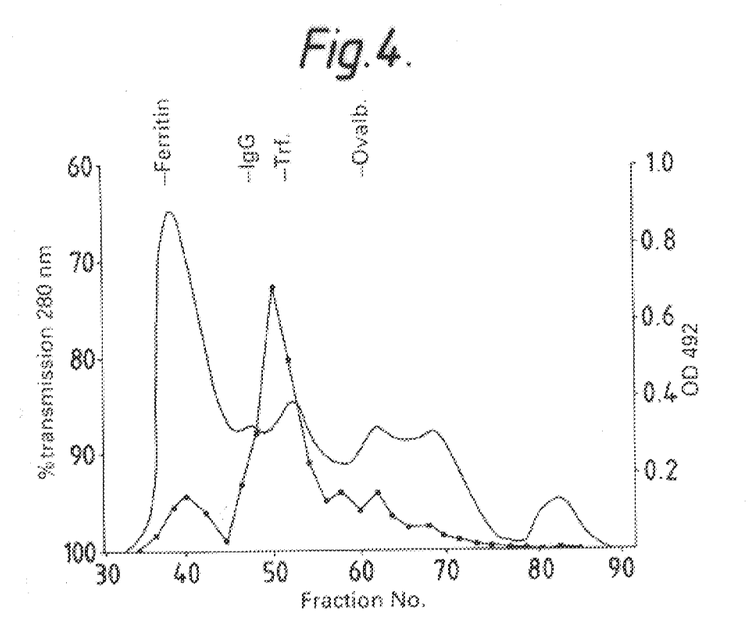

In order to investigate any association of 5T4 antigen with itself or any other protein, DOC solubilised StMPM was subjected to gel filtration over S200 Sephacryl run in the presence of detergent, and the fractions assayed for 5T4 reactivity in ELISA. 5T4 antigen eluted with an apparent molecular weight of 120 kD, although there was a small peak of reactivity in the void volume (FIG. 4).

Antigenicity

Isolated StMPM membranes were digested with trypsin, pronase, neuraminidase or N-glycanase, the components solubilised and subjected to immuno-dot assay. Both proteases and N-glycanase destroyed 5T4 antigenicity, whilst neuraminidase did not (Table IV). The effects of various fixatives on 5T4 antigenicity as expressed by Tera-2 cells was assessed by solid-phase radiobinding assay. Neither Bouins' fixative, buffered formalin, gluteraldehyde or absolute ethanol were found to significantly affect 5T4 binding index relative to PBS control (data not shown).

DETAILED DESCRIPTION OF THE FIGURES

FIGS. 1A–1F

Colour plate. Expression of 5T4 antigen in placenta. Immunohistology of term chorionic villi (a,c,e) or amniochorion (b,d,f) with normal mouse serum (e,f) or monoclonal antibodies 1D2 (a) E316 (b) or 5T4 (c,d) followed by rabbit anti-murine immunoglobulin peroxidase conjugate. Sections were counterstained with haemalum (BDH). IVS, intervillous space; St, syncytiotrophoblast; VS, villous stroma; AE amniotic epithelium; AM, amniotic mesenchyme; CL, chorion laeve; DP, decidua parietalis. 5T4 shows specific labelling of villous trophoblast and extravillous cytotrophoblast of the chorion laeve as well as amniotic epithelium. Positive control mAb 1D2 labels all cell types; mAb H316 labels trophoblast of the chorion laeve and amniotic epithelium. Normal mouse serum shows no labelling.

FIG. 2

Immunoprecipitation of 5T4 molecules from StMPM. Autoradiography of SDS-PAGE analysis of 5T4 immunoprecipitates of NP-40 solubilised 125I-lactoperoxidase labelled StMPM (lane 1) and following digestion with N-glycanase (lane 2). 8% gel.

FIG. 3

Fluorography of reduced SDS-PAGE of 5T4 immunoprecipitates from StMPM labelled with NaB$^3$H4 following treatment with either periodate (PI) or galactose oxidase and neuraminidase (GO-N). 10% gel. T is total radiolabelled glycoprotein following periodate treatment.

FIG. 4

Gel filtration of 5T4 antigenic molecules. Solubilised StMPM protein fractionated over S200 Sephacryl in the presence of detergent. Fractionated 5T4 antigenicity assessed in ELISA.

TABLE I

REACTIVITY OF MONOCLONAL ANTIBODY 5T4 WITH NORMAL HUMAN TISSUE AS ASSESSED BY IMMUNOHISTOLOGY OF FROZEN SECTION.

| Tissue | Result |
|---|---|
| Placenta | +++ Villous trophoblast and amnion |
| Brain | – |
| Ovary | – |
| Testis | – |
| Skeletal muscle | – |
| Heart | – |
| Lung | – |
| Bronchus | – |
| Liver | – |
| Spleen | – |
| Kidney | + Glomeruli |
| Bladder | + Epithelium |
| Small intestine | + Villous epithelium |
| Uterus | + Endometrial glands |
| Cervix | + Endocervical glands |
| Skin | + Basal epidermis |

TABLE II

EXPRESSION OF 5T4 AND OTHER TROPHOBLAST ANTIGENS BY NON-PREGNANCY TISSUES AS ASSESSED BY IMMUNODOT.

| | Immunodot titre | | |
|---|---|---|---|
| Tissue | 5T4 | H317 | 1D2 |
| Term placenta | 50 ng | 200 ng | 50 ng |
| Brain | >50 ug | >50 ug | 200 ng |
| Muscle | >50 ug | >50 ug | 200 ng |
| Kidney | >50 ug | >50 ug | 100 ng |
| Liver | >50 ug | >50 ug | 100 ng |
| Ovary | >50 ug | >50 ug | 100 ng |
| Testis | >50 ug | >50 ug | 100 ng |

Results of immunodot expressed as minimum antigen concentration required to produce a positive result.

TABLE III

REACTIVITY OF MAB 5T4 WITH NORMAL CELLS AND TRANSFORMED CELL LINES IN CELL-SURFACE IMMUNOFLUORESCENCE AND RADIOBINDING ASSAY.

| | | | RESULT | | |
|---|---|---|---|---|---|
| Cell | Origin | Type | Fluorescence | Binding index | Reference |
| AV-3 | Amnion | Epithelial | + | 3.1 | McLaughlin et al., 1982. |
| WISH | Amnion | Epithelial | nt | (3.4) | Gift of |

TABLE III-continued

REACTIVITY OF MAB 5T4 WITH NORMAL CELLS AND TRANSFORMED CELL LINES IN CELL-SURFACE IMMUNOFLUORESCENCE AND RADIOBINDING ASSAY.

| Cell | Origin | Type | Fluorescence | Binding index | Reference |
|---|---|---|---|---|---|
| MRC-5 | Fibroblasts | Embryonic | + | 3.8t | P. McLaughlin, Liverpool Jacobs et al., 1970. |
| Flow 7000 | Fibroblasts | Embryonic | nt | (2.9) | Gift of P. McLaughlin, Liverpool |
| I407 | Intestine | Embryonic | + | nt | Gift of A. Smith, Clatterbridge |
| PBL | Peripheral blood | Leucocytes | – | nt | (1) |
| UC729/6 | B-cell | Myeloma | – | nt | Gift of A. Smith, Liverpool. |
| HMI | " | Myeloma | – | nt | Gift of A. Smith, Liverpool |
| RAJI | " | Lymphoblastoid | – | 1.2 | Pulvertaft, 1964. |
| BSM | " | Lymphoblastoid | – | 1.2 | Gift of Dr. C. Graham, Oxford. |
| Daudi | " | Burkitt's lymphoma | – | 1.2 | Klein et al., 1967. |
| B27 | " | EBV-lymphoblastoid | – | 1.1 | Gift of Prof. C. Hart, Liverpool. |
| Molt-4 | T-cell | Leukaemia | – | nt | Minowada et al., 1972. |
| K562 | " | Erythroleukaemia | – | 1.2 | Andersson et al., 1979. |
| GCCM/15 | Brain | Glioma | + | 5.2t | Gift of Dr. T. Alderson, London. |
| Hep-2 | Larynx | Carcinoma | + | (5.0) | Moore et al., 1955. |
| HN2 | Larynx | " | + | (1.5)t | Easty et al., 1981 |
| HN4 | Larynx | " | + | 3.0t | Easty et al., 1981 |
| HN1 | Tongue | " | + | 2.9t | Easty et al., 1981 |
| HN5 | Tongue | " | + | 3.1t | Easty et al., 1981 |
| IPT | Bronchus | " | – | 1.2t | Kumar et al., 1983. |
| IPTV2 | Bronchus | " | – | 1.3t | Walker et al., 1984 |
| N417 | Small lung | " | – | 1.2 | Gift of Dr. T. Alderson, London |
| 6CT | Cervix | " | + | 2.2 | Daniels et al., 1984 |
| ElCo | Breast | " | nt | 1.7 | Gift of P. McLaughlin, Liverpool |
| EJ | Bladder | " | + | nt | O'Toole et al., 1983. |
| A431 | Vulva | " | + | 4.2t | Fabricant et al., 1977. |
| HT29 | Colon | " | + | 3.4t | Gift of A. Smith, Liverpool. |
| Mawi | Colon | " | – | nt | Gift of A. Smith, Liverpool. |
| Chang | Liver | " | nt | (4.1) | Gift of P. McLaughlin, Liverpool |
| Tera-1 | Testis | Teratocarcinoma | + | (2.6) | Fogh and Trempe, 1975. |
| Tera-2 | Testis | Teratocarcinoma | + | 4.2 | Thompson et al., 1984. |
| 2102Ep | Testis | Teratocarcinoma | + | (3.5) | Andrews et al., 1984. |
| PA-1 | Ovary | Teratocarcinoma | + | (4.1) | Zeuthen et al., 1980. |
| BeWo | Chorion | Choriocarcinoma | + | (5.2) | Patillo and Gey, 1968. |
| JAr | Chorion | Choriocarcinoma | + | (4.9) | Patillo et al., 1971. |
| SK-NEP | Kidney | Wilm's-tumour | – | (1.2) | Fogh and Trempe, 1975. |
| Gos.1.8.1 | Kidney | Wilm's-tumour | – | (1.4) | Gift of Dr. C. Graham, Oxford. |
| GM3808 | Kidney | Wilm's-tumour | + | (5.1)t | Gift of Dr. T. Alderson, London. |

Cells harvested with EGTA alone or EGTA-trypsin (t). Cells incubated with mAb 5T4 followed by fluorescein-conjugated sheep anti-murine Ig (immunofluorescence) or $^{125}$I rabbit anti-mouse immunoglobulin (Binding assay). Results expressed as positive immunoflourescence or binding index relative to negative control. Standard deviation of four replicates was less than 10%; variation between 2–4 experiments was generally less than 10%. Figures in brackets represent results from a single experiment. (1) PBL isolated from peripheral blood by centrifugation over Ficoll-hypaque. nt = not tested.

TABLE IV

EFFECT OF ENZYMIC DIGESTION ON 5T4 ANTIGENICITY AS ASSESSED IN IMMUNODOT

| Enzyme | 5T4 titre |
|---|---|
| PBS | 80 ng |
| Pronase | >10 ug |
| Trypsin | >10 ug |
| Neuraminidase | 80 ng |
| N-glycanase | >10 ug |

StMPM protein incubated overnight at 37° C. with appropriate enzymes or PBS (as control for auto-degradation) and dot-blotted onto nitrocellulose. Results expressed as minimum protein dot concentration required to produce a positive result.

The following experimental data describes tests on the immunohistological distribution of 5T4 antigen in a range of neoplastic and non-neoplastic tissues.

Immunohistochemistry:

A panel of normal, non-neoplastic and neoplastic tissues were used. Fresh tissue samples were quenched in isopentane, cooled in liquid nitrogen for a few minutes until viscous. 6 micron thick cryostat sections were cut, air dried for 10 minutes and then fixed in acetone. An avidin-biotin immunoperoxidase technique was employed for the screening of the hybridoma culture supernatant 5T4.

Specifically sections were washed in two changes of tris buffered saline (TBS) pH 7.6 and then covered with 10% normal horse serum in TBS for 20 minutes. After draining, the slides were incubated with neat culture supernatant for 30 minutes in a moist chamber. Following 3 washes in TBS (5 minutes each) biotinylated anti mouse Ig (Vector Laboratories) diluted 1/250 in TBS containing 10% normal human serum was applied. After 30 minutes incubation in the moist chamber the slides were washed 3 times with TBS. Sections were then covered with avidin-biotin peroxidase complexes reagent (Vector Laboratories) and incubated for 50 minutes. After three washes in TBS peroxidase was visualised using a freshly prepared and filtered solution of diaminobenzidine tetrahydrochloride (DAB-Sigma) in TBS containing 0.03% hydrogen peroxidase. (6 minutes). Sections were washed in tap water and counter stained in Coles haematoxylin, dehydrated, cleared and mounted (Ralmount-R. A. Lamb). The immunohistochemical results were interpreted with reference to a set of controls run in parallel with each test. These included sections treated with DAB only to show endogenous peroxidase, omission of the primary antibody and replacement of the primary antibody with one of the same class but of unrelated specificity. In addition some sections of tumour were incubated with monoclonal antibodies to CEA, HCG and placental alkaline phosphatase for comparison with the antigen distribution recognised by monoclonal antibody (MAb) 5T4. Reactivity of MAb 5T4 with fixed and paraffin wax embedded material was also assessed by immunoperoxidase.

Results

The distribution of positive reactions with MAb 5T4 in normal and non neoplastic tissues is summarised in Table I. The villous syncytiotrophoblast from first and third trimester placentae and an ectopic (tubal) pregnancy showed strong membrane positivity. Placental site trophoblast displayed both membrane and cytoplasmic reactions. The stroma of chorionic villi and foetal blood vessels were negative.

In the non-neoplastic tissues examined weak or moderate reactions were found in the basal layer of stratified squamous epithelium (cervix, oesophagus and skin), glandular epithelium of endocervix and endometrium, mucosal glands of stomach and large intestine and some excretory ductal epithelium of pancreas. Whilst the tissues of the lung were usually negative, focal weak labelling of cuboidal epithelium lining a bronchiole was seen. All components of non-neoplastic or normal ovary, liver and testis were unreactive with MAb 5T4.

Table II summarises the distribution of MAb 5T4 in neoplastic tissues. Many of the malignant epithelial tumours displayed positive reactions in the neoplastic cells. Of note, were carcinomas of breast (5/5), lung (5/5), stomach (6/7) and pancreas including one of the ampulla of Vater (4/4). Also positive, albeit in only a limited number of cases available, were carcinomas of endometrium and cervix.

The majority of colonic adenocarcinomas were negative, positivity in 3/12 was confined to only a few tumour cells and was weak.

Cystadenocarcinomas of the ovary produced variable reactions. In three of the four positive cases the majority of tumour cells were positive, and in the other the majority were negative.

In the testes all classical seminomas were negative; only a seminoma with syncytiotrophoblast-like giant cells and admixed with embryonal carcinoma being positive. All anaplastic germ cell tumours of the testis showed variable positive reactions. Where syncytiotrophoblast was present this was strongly positive. Generally embryonal carcinoma and yolk sac structures were only feintly positive. This ranged from the majority of tumour cells being positive (1 case) to a minority (1 case). Undifferentiated mesenchyme may also be positive.

The cystic epithelium of mature teratomas often displayed a focal weak to moderate reaction.

Syncytiotrophoblast of choriocarcinomas and a complete hydatidiform mole was strongly positive. Much of the trophoblast of placental site tumours showed moderate or strong labelling on both cell membranes and within the cytoplasm. Single examples of fibrosarcoma and leiomyosarcoma showed that whilst most tumour cells were negative, there were focal and weak reactions in a few cells. Malignant melanomas (2) and malignant lymphomas (3) were negative.

The stroma of some tumours showed weak and focal reactions. This was also noted in the endothelium lining mainly small blood vessels in many tissues and tumours.

The cellular location of binding with mAb5T4 in tumours may be either membranous or cytoplasmic or a combination of both. Heavy membrane-bound location is a particular feature of syncytiotrophoblast. Cytoplasmic reactivity was predominant in pancreatic carcinomas. In gastric and breast carcinomas both types of pattern were present. MAb 5T4 was unreactive with fixed and paraffin wax embedded tissue sections of villous trophoblast of term placentae.

Comment

MAb 5T4 gives reactions in trophoblast which are similar to other antitrophoblast antibodies. However our detailed immunohistochemical analysis tends to suggest that the antigen recognised is distinct from HCG,HPL,PLAP and those which react with mAb 18A/C4 and 18B/A5 (Loke, University of Cambridge). Some of the differentiating immunohistochemical features are summarised below.

Unlike antibodies to HCG, 5T4 will react with some non-HCG producing tumours and gives intense reactions wit h syncytiotrophoblast of term placenta. Antibodies to both HCG and HPL are unreactive with the basal layer of stratified squamous epithelium and normal or non-neoplastic endocervical glands.

Seminomas, usually positive with mAbs against the Nagao isozyme of PLAP, (egH17/E2) were almost all negative using 5T4. (The one case that showed some positivity was a seminoma containing syncytiotrophoblast giant cells, admixed with embryonal carcinoma. MAb 5T4 in contrast to mAbs reactive with the Regan isoenzyme of PLAP was usually negative with bronchiolar epithelium. Unlike both 18A/C4 and 18B/A5 antibodies mAb 5T4 did not react with villous cytotrophoblast.

The failure of mAb 5T4 to react in fixed and routinely processed paraffin sections is a characteristic of some other reported antibodies directed against membrane-associated antigens, notably anti-PLAP, 18A/C4 and 17.1A antibodies.

TABLE V

Results of Immunohistochemical Distribution of
Monoclonal Antibody 5T4 in normal and non-neoplastic tissues

| Tissue/Organ | Morphology | Number positive | Intensity of staining | Distribution/Comments |
|---|---|---|---|---|
| Cervix | Cervicitis/ squamous metaplasia | 4/4 | + | Endocervical glands, positive in ¾ and basal layer of squamous epithelium in ⅔ (squamous epithelium not present in 1 case |
| Endometrium | Non-neoplastic from choriocarcinoma and | 1/2 | + to ++ | Endometrial glands positive from case of choriocarcinoma and negative in normal pregnancy. Endo-metrial stroma and myometrium negative |
| Intestine, large | Normal or non-neoplastic mucosa | 3/6 | +/− to + | Mucous secreting epithelium weakly positive and some constituents of lamina propria. Most negative. |
| Intestine, small, adult | Normal | 0/1 | | |
| Intestine small, fetal | | 0/1 | | |
| Kidney | Non-neoplastic | 0/2 | | Tubules, negative but faint +/− of probable endothelial cells in glomeruli Glomeruli only present in 1 case |
| Liver | Non-neoplastic | 0/4 | | All components negative |
| Lung | Non-neoplastic lung taken from primary tumours | 1/4 | + to ++ | Only focal staining of cuboidal cells lining a bronchiole. Otherwise negative |
| Lung | Non-neoplastic lung taken from metastases | 1/5 | ?+++ | Difficult to assess whether these are alveolar lining cells, type II pneomocytes or degenerate tumour since from a case of choriocarcinoma other-wise lung parenchyma in other cases is negative |
| Lymph node | Non-specific reactive changes | 1/1 | +/ to + | Clusters of cells in sinusoids faintly positive, probably endothelial cells and histiocytes. |
| Oesophagus | Non-neoplastic | 2/2 | + | Basal layer of stratified squamous epithelium |
| Ovary | Non-neoplastic including corpus luteum, corpore albicontra and stroma | 0/4 | | Almost all negative apart from faint focal +/− of stromal cells. Surface epithelium and follicles not seen. |
| Prostate gland | Hyperplasia | 1/1 | +/− to + | Focal of glandular epithelium, most negative |
| Pancreas | Normal or non-neoplastic | 3/3 | + | Focal, faint staining of small collecting duct cuboidal epitheliuin and mucus secreting epithelium. Most acinar cells negative but focal +/− |
| Seminal vesicles | Normal | 1/1 | +/ to + | Focal of epithelium. Most negative |
| Skin | Epidermis | 2/2 | + | Faint, focal staining of basal layer of stratified squamous epithelium. |
| Spleen | Non-specific reactive changes | 0/3 | | All negative in white pulp. 1 case show; vascular endothelium faintly positive in red pulp |
| Stomach | Non-neoplastic mucosa | 2/4 | + | |
| Testis | non-neoplastic | 0/2 | | Seminiferous tubules, spermatogoria, mature sperms, sertoli cells, Leydig cells, all negative |
| Thymus | fetal | 0/1 | | |
| Thyroid gland | Follicular collio nodule | 1/1 | +/− to + | Focal staining of cells lining follicles. Most negative. Colloid negative |
| Trophoblast | Placenta, early | 3/3 | + to +++ | Syncytiotrophoblast + to +++ cyto-trophoblastand fetal vessels negative |
| Trophoblast | Placenta, term | 2/2 | +++ | Strong staining of syncytiotrophoblast membrane. Maternal and fetal vessels negative |
| Trophoblast | Ectopic pregnancy | 1/1 | + to +++ | Syncytiotrophoblast strong staining. weaker staining of placental site trophoblast. Stroma of chorionic villi negative |

TABLE VI

Results of Immunohistochemical Distribution of
Monoclonal Antibody 5T4 in Neoplastic Tissues

| Tissue/Organ | Morphology | Number positive | Intensity of staining | Distribution/Comments |
|---|---|---|---|---|
| Ampulla of Vater | Invasive adenocarcinoma | 1/1 | +++ | Focal staining of tumour acini Membrane and cytoplasmic |
| Bladder | Poorly differentiated carcinoma with squamous differentiation | 1/1 | ++ | Focal positivity of some tumour cells membrane and cytoplasmic. Most tumour cells negative |
| Brain | Glioblastoma multiforme | 0/1 | | |
| Breast | Invasive adenocarcinoma | 5/5 | + to ++ | Usually membrane and cytoplasmic staining of tumour cells. Occasional +/− 'wispy' staining of stroma |
| Cervix | Invasive squamous carcinoma | 1/1 | +++ | Cytoplasmic ⅗ membrane in most tumour cells, endocervical glands show ++ to +++ and + to ++ stromal cells. |
| Colon | Invasive adenocarcinoma | 3/12 | + | Focal, of few tumour cells only. Weak +/− to + of stroma and non-neoplastic large bowel mucosal glands |
| Colon | Tubulovillous adenoma | 1/1 | ++ | Mainly membrane (mucosal surface) with some cytoplasm. |
| Endometrium | Invasive adenocarcinoma | 1/1 | + to +++ | Small groups of cells +++ membrane, focal ++ staining of undifferentiated and multinucleate cells. |
| Endometrium | MMMT* | 1/1 | + to +++ | Focal, mainly cytoplasmic. Large clumps of tumour cells negative |
| Kidney | Clear cell adenocarcinoma | 1/1 | ++ | Focal membrane and cytoplasm of tumour cells |
| Liver | Metastatic carcinoid tumour | 0/1 | | |
| Lung | Squamous carcinoma | 2/2 | + to ++ | Most of tumour cells positive, Membrane and cytoplasm. Tumour debris positive in one case |
| | Large cell, undifferentiated | 1/1 | + | Most tumour cells positive, membrane and cytoplasm, patchy staining of the stroma surrounding tumour. |
| | Giant cell carcinoma | 1/1 | +++ | Most tumour cells positive, membrane |
| | Broncho-alveolar carcinoma | 1/1 | + | Most tumour cells positive, cytoplasmic |
| | Metastatic leiomyo-sarcoma | 1/1 | + | Focal, membrane and cytoplasm of tumour cells + of collagenised stroma |
| Lymph node | Lymphoma Non-Hodgkins, (including x of large bowel) | 0/3 | | |
| Oesophagus | Squamous carcinoma | 1/1 | + to ++ | Focal, most tumour cells negative |
| Ovary | Brenner Tumour (in mucinous cystadenoma) | 1/1 | + | Clusters of Brenner tumour only positive, cytoplasm |
| Ovary | Granulosa cell tumour | 0/1 | | |
| | Cystadenoma | 0/3 | | Weak +/− focal of mucin |
| | Cystadenocarcinoma various **** | 4/7 | ++ to +++ | Positive tumours, both membrane and cytoplasm. In 3 cases most tumour cells positive and approx. 5% of tumour cells poaitive in 1 case. Negative tumours - serous papillary (xl) mucinous (xl), poorly differentiated (xl) |
| | Teratoma, solid | 1/1 | +/− to +++ | Basal layer of squamous epithelium +/−, respiratory epithelium +, focal in mucin secreting cells. Mesenchyme and chondrocytes +/− to + Acini ++ to +++ |
| Pancreas | Invasive adeno-carcinoma | 3/3 | +/− to ++ | Focal, mainly cytoplasm with little membrane. Many tumour cells negative Stroma +/− to ++ |
| Skin | Basal cell carcinoma | 0/1 | | |
| | Malignant melanoma | 0/2 | | In one case, a very few cells faintly positive, otherwise all tumour cells negative. |
| Soft tissue | Fibrosarcoma | 1/1 | + | Focal positivity in a few cells. |
| Stomach | Invasive adenocarcinoma | 6/7 | +/− to ++ | Membrane and cytoplasm in tumour cells. Variable reaction of non-neoplastic gastric mucosas negative or +/− to ++. Extracellular mucin positive in two cases. Sometimes stroma surrounding tumour +/− to ++, Rarely cells in lamina propria positive |

TABLE VI-continued

Results of Immunohistochemical Distribution of
Monoclonal Antibody 5T4 in Neoplastic Tissues

| Tissue/Organ | Morphology | Number positive | Intensity of staining | Distribution/Comments |
|---|---|---|---|---|
| Testis | Seminoma | 1/5 | + to ++ | Focal staining of tumour cells in a seminoma with syncytiotrophoblast giant cells and embryonal carcinoma syncytiotrophoblast cells faintly positive |
| | Teratoma mature cystic (in testis) | 3/4 | +/− to ++ | Focal + of basal layer stratified squamous epithelium and columnar epithelium. Mucin secreting goblet cells ++. + immature mesenchyme |
| | Teratoma, mature cystic, metastatic from testis to lung/ lymph node | 0/3 | | |
| Teratoma | Anaplastic germ cell tumours, including three metastases, two MTI, one of which is metastatic | 7/7 | +/− to +++ | Trophoblast +++, M. Embryonal carcinoma/yolk sac tumour + Undifferentiated tumour, possibly neurol, ++. Note, these tumours are variable in their reactions and in some many tumour cells are negative |
| Thyroid | Adenocarcinoma metastatic to thyroid, (unknown primary) | 0/1 | | |
| Trophoblast | Choriocarcinoma (×2 in uterus ×1 in lung ×2 in brain) | 5/5 | + to +++ | Syncytiotrophoblast ++ to +++, M. Cytotrophoblast + to ++ in one case |
| | Placental site Trophoblast tumour | 2/2 | ++ to +++ | Most tumour cells, mainly membrane, some cytoplasm |
| | Hydatidiform mole | 1/1 | + to +++ | Syncytiotrophoblast +++ membrane staining; faint + staining of cyto-trophoblast. Stroma of chorionic vill negative |

*MMMT = Malignant, Mixed Mullerian Tumour
**including serous cystadenocarcinoma × 2
mucinous cystadenocarcinoma × 1
metastatic ovarian carcinoma in lymph node × 1

CERVICAL CANCER STUDIES

The reactivity of the 5T4 mAb with invasive carcinoma of the cervix [refer to Table VI above] has prompted a comprehensive investigation of this malignancy and the premalignant changes which can be monitored because of the accessibility to the cervix. Cervical carcinoma arises from dysplastic precursor lesions in the reserve cells in the basal layer of the stratified metaplastic epithelium. These areas develop from proliferating basal cells which have undergone some form of transformation, and gradually spread throughout the whole epithelium. Cervical carcinomas thus develop from a series of atypical changes which progress in continuum to a stage of carcinoma in situ. This is probably the final premalignant state before the lesion invades the underlying stroma becoming microinvasive. The dysplastic variations have been categorised as a series of changes in cervical intraepithelia neoplasia (CIN). They have been graded from 1-3, with CIN 1 representing less than a third of the dysplastic involvement, located in the basal layer. CIN 2 with a third to two thirds involvement, and CIN 3 two thirds to full thickness involvement, equivalent to carcinoma in situ. At any stage, the lesion may regress back to normality. 90% of cervical neoplasms are squamous cell carcinomas and have a contrasting aetiology and of epidemiology to adenocarcinomas (present in nulliparous women) which comprise the remaining 8–10%.

Preparation of tissue for immunohistology (I.H. Frozen Specimens

Placental tissue was washed in PBS (phosphate buffered saline). 1 cm$^3$ of tissue was then embedded in OCT compound and snap-frozen by immersing the specimen in $CO_2$ ice with isopentane, within 1 hour post partum. Frozen cervical specimens were selected from a store at the Royal Liverpool Women's Hospital (RLWH). These samples, from cone or punch biopsies routinely submitted for histology, were embedded in polycel, snap-frozen and stored at −70° C. The specimens were cut at 7 μm thick using a cryostat and placed on slides (cleaned with ethanol and coated with poly-L-lysine). The pathological assessment was obtained from the records of examination of the specimens subjected to fixation in formal buffered saline, dehydration wax embedding and haemotoxin/eosin staining.

Immunohistology

The method described by Bulmer & Sunderland (1983) was used for placental sections but modified for cervical sections. Briefly, the slides were dried at room temperature for 30 minutes before being washed in PBS. Endogenous peroxidase activity was blocked in 3% $H_2O_2$ in ethanol, followed by 3 washes 2.5% sucrose/PBS, and 2 washes 1% Bovine Serum Albumin (BSA)/PBS. The sections were incubated with 10% normal goat serum (NGS) (in 1% BSA/PBS) for 20 minutes before the application of the first layer Ab. All reagents were microfuged at 14,000 g for 10 minutes to remove debris before use. The first layer test mAb was applied (ascites fluid diluted 1/100 in 1% BSA/PBS) and incubated for 1 hour at room temperature in a moist box. Subsequently, each slide was washed individually×3 in 1% BSA/PBS before having the second layer peroxidase conjugated rabbit anti-mouse (R anti-MIg) (Dako) diluted 1:50 in 1% BSA/PBS +10% normal human serum (NHS). After 1 hour incubation (same conditions as before), the slides were washed 2×1% NHS, 1% BSA/PBS and developed using 3'3' diaminobenzidine, 5 µg/10 mls PBS +0.02% $H_2O_2$). The reaction was stopped after 10 minutes by rinsing with tap water. The slides were counterstained using Meyer's Haemalin dehydrated by passing up graded alcohols, fixed in xylene and mounted. All experiments were performed using positive W6/32) and negative (10.2.16) control ascites fluid.

Detection of 5T4 expression in cervical tissue

Tissue sections were selected on the basis of routine diagnosis, being placed into the appropriate groups according to the pathology of the epithelium. The groups were categorised as follows: normal, metaplastic, HPV infected, CIN 1, CIN 2 or CIN 3, with or without HPV infection, invasive carcinoma and common non-malignant cervical inflammatory disorders. Over a 100 biopsy specimens were investigated and each experiment was performed with a positive and negative control (W6/32 and 10.2.16 respectively), read independently by two observers—some material was poorly preserved and not included in the summary. Placental villous sections were included in each experiment to ensure that the procedure was working optimally. The degree of labelling was assessed as anything above that shown in the negative control, eliminating the possibility of false positives becoming included into the study. A subjective estimation of the intensity of the labelling was also made. Experiments were repeated at least once on greater than 50% of the specimens.

RESULTS

5T4 Expression in cervical biopsy frozen sections

Table VII summarises the extent of 5T4 labelling from the basal epithelium to the surface in 66 cone or punch biopsies from the ectocervix. The data can be grouped in several categories. The sections of "normal" ectocervix, squamous metaplasia and HPV infection without evident dysplasia exhibited an overlapping phenotype in intensity and range of distribution of 5T4 antigen. 9/17 showed labelling confined to the basal cells of the epithelium; 6 showed faint labelling throughout the epithelial layers and only 2 demonstrated significant labelling to level C3. There was labelling associated with the stromal elements to the same degree as the basal layer: columnar epithelium and glands when present were labelled. These results are in the range of those described for cervical tissue in a previous immunohistological study of 5T4 expression in normal and neoplastic tissues.

The above arbitrary grouping shows no obvious differences from the specimens in the CIN 1 category. The latter is characterised by the appearance of atypical nuclei located in the lower third of the epithelium. Where the morphology was preserved in the frozen sections, it was frequently noted that the 5T4 labelling was located in the parabasal layers corresponding to the area of dysplasia.

From the data on Table VII, it is apparent that there is a progression through CIN 2 and CIN 3 to a more extensive pattern and intensity of labelling with 5T4 monoclonal antibody. The staining is of higher intensity than in that detected generally in the non-dysplastic or CIN 1 specimens. All the CIN specimens frequently exhibited stromal labelling with an intensity to the basal layers. Where the morphology of dysplastic cells could be assessed, it was evident that from the CIN 2 (HPV) and CIN 3 categories that the specific 5T4 labelling associated with the abnormal cells. 14/15 CIN 3 showed labelling from the basal layer to just below the surface epithelium; 9/15 exhibited labelling along the surface. 5/5 examples of squamous cell carcinoma showed positive intense labelling of the malignant cells and surrounding stroma. The final group of miscellaneous conditions includes hyperplasia, chronic inflammation, cervicitus, acanthotic epithelium and radiation induced atypia. These specimens were selected on the basis of their conventional pathology and exhibited a range of labelling. The inflammatory infiltration response did not increase 5T4 expression per se; the single example of acanthotic epithelium was clearly labelled as were 2/3 of the hyperplastic epithelia. This arbitrary grouping shows some tendency to higher levels of 5T4 expression in the centre layers but appears different from the CIN 2 and CIN 3 groupings.

A new approach using a tumour marker specific for cervical cancer may revolutionise current methods for screening, by offering the potential for the tumour specific Ag to be detected in serum and mucous samples and solubilised biopsies.

Observing the 5T4 antigenic distribution over a wide range of malignant and premalignant conditions in cervical cancer, a consistent pattern of staining for specific pathological disorders was evident. Normal cervical epithelium, one of the 'specialised' epithelia, showed faint reactivity localised to the reserve cells only. CIN, being the progressive transformation from normal to the malignant state, demonstrated an increased pattern of epithelial labelling corresponding to the severity of the dysplasia. Labelling of the stroma, glands and vessel endothelium also increased as the malignant potential progressed, with no evidence of reactivity with inflammatory cells. Invasive carcinoma showed strong staining of the malignant cells and the intervening stroma. Anaplastic tumours showed patchy variable labelling which may reflect the transformed cells' ability to modulate their morphology and antigenic characteristics. The labelling of the atypical cells is consistent with the theory of the malignant lesion commencing from the basal layers and spreading to the surface.

The quantitative assessment, of 5T4 antigenicity in cervical smear material using radio or other immunoassay with 5T4 monoclonal antibodies may be used as a means of assessing the degree of dysplastic cells in a specimen. This procedure can be highly efficient in mass screening and assigning further investigative procedures.

TABLE VII

5T4 ANTIGEN EXPRESSION IN NON-DYSPLASTIC AND DYSPLASTIC CERVICAL CONDITIONS

| PATHOLOGY | SPECIMEN NUMBER | EPITHELIAL LAYER | | | | |
|---|---|---|---|---|---|---|
| | | C1 | C2 | C3 | C4 | C5 |
| Normal ectocervix | 1 | – | –+ | + | ++ | ++ |
| | 2 | –+ | –+ | –+ | –+ | ++ |
| | 3 | – | – | – | – | + |
| | 4 | –+ | –+ | –+ | –+ | ++ |
| | 5 | – | – | – | – | + |
| | 6 | – | – | – | – | + |
| | 7 | – | – | – | – | + |
| | 8 | – | – | – | –+ | ++ |
| | 9 | – | – | – | – | + |
| Squamous metaplasia | 10 | – | – | – | – | – |
| | 11 | – | – | – | – | + |
| | 12 | –+ | –+ | –+ | + | + |
| HPV without CIN | 13 | –+ | –+ | –+ | + | + |
| | 14 | – | – | – | – | + |
| | 15 | – | – | – | – | + |
| | 16 | – | – | + | + | ++ |
| | 17 | –+ | –+ | –+ | + | ++ |

TABLE VII-continued

5T4 ANTIGEN EXPRESSION IN NON-DYSPLASTIC AND DYSPLASTIC CERVICAL CONDITIONS

| PATHOLOGY | SPECIMEN NUMBER | EPITHELIAL LAYER | | | | |
|---|---|---|---|---|---|---|
| | | C1 | C2 | C3 | C4 | C5 |
| CIN 1 | 18 | − | − | − | + | ++ |
| | 19 | − | − | − | − | ++ |
| | 20 | − | − | − | − | −+ |
| | 21 | − | − | − | −+ | + |
| | 22 | − | − | − | −+ | + |
| | 23 | − | − | − | − | + |
| CIN 1 with HPV | 24 | − | − | − | − | ++ |
| | 25 | + | + | + | + | + |
| | 26 | − | − | − | + | ++ |
| | 27 | − | − | −+ | + | ++ |
| | 28 | + | + | + | + | + |
| | 29 | −+ | −+ | −+ | −+ | ++ |
| CIN 2 | 30 | − | − | − | − | + |
| | 31 | − | + | + | + | + |
| | 32 | − | − | ++ | ++ | ++ |
| | 33 | − | + | + | + | + |
| | 34 | + | + | + | + | ++ |
| CIN 2 with HPV | 35 | + | + | + | ++ | ++ |
| | 36 | − | + | + | ++ | ++ |
| | 37 | + | + | + | + | ++ |
| CIN 3 | 38 | + | ++ | ++ | ++ | ++ |
| | 39 | + | + | ++ | ++ | ++ |
| | 40 | − | + | + | ++ | ++ |
| | 41 | − | + | + | ++ | ++ |
| | 42 | + | + | + | + | ++ |
| | *43 | − | + | + | ++ | ++ |
| | 44 | ++ | ++ | ++ | ++ | ++ |
| | 45 | − | + | + | + | + |
| | 46 | + | + | ++ | ++ | ++ |
| CIN 3 vith HPV | 49 | + | + | + | ++ | ++ |
| | 50 | + | + | ++ | ++ | ++ |
| | 51 | −+ | − | − | + | ++ |
| | 52 | + | + | + | + | ++ |
| Invasive Carcinoma | 53 | Epithelial layers not present tumour in stroma | | | | ++ ++ ++ ++ ++ |
| Hyperplasia | 58 | + | + | + | + | ++ |
| | 59 | − | − | −+ | −+ | −+ |
| | 60 | + | + | + | + | + |
| Chronic Inflammation | 61 | − | − | − | − | ++ |
| | 62 | + | −+ | −+ | −+ | + |
| Cervicitis & glandular atypia | 63 | −+ | −+ | −+ | −+ | −+ |
| | | − | − | + | + | ++; |
| Acanthotic Epithelium | 65 | + | + | + | + | + |
| Radiation induced atypia | 66 | − | − | − | − | − |

REFERENCES

Andersson, K., Nilsson, R. and Gahmberg, C. G. (1979) K562- A human erythroleukamia cell line. Int.J.Cancer., 23, 143.

Andrews, P. W., Damjanov, I., Simon, D. and four others (1984). Pluripotent embryonal carcinoma clones derived from the human teratocarcinoma cell line Tera-2. Lab. Invest., 50, 147.

Axelsson, B., Kimura, A., Hammarstrom, S., Wigzell, H., Nilsson, K. and Mellstedt, H. (1978) Helix pomatia A haemagglutinin: selectivity of binding to lymphocyte surface glycoproteins on T cells and certain B cells. Eur.J.Immunol., 8, 757.

Bohn, H., Dati, F. and Luben, G. (1983) Human trophoblast specific products other than hormones. In Biology of trophoblast, Loke, Y. W. and Whyte, A. (eds.), p318, Elsevier: Amsterdam.

Bramwell, M. E., Ghosh, A. K., Smith, W. D., Wiseman, G., Sprigger, A. I. and Harris, H. (1985). New monoclonal antibodies evaluated as tumour markers in serous effusions. Cancer, 56, 105.

Bulmer, J. N. and Sunderland, C. A. (1983) Bone-marrow origin of endometrial granulocytes in the early human placental bed. J.Reprod.Immunol., 5, 383.

Burchell, J., Durbin, H. and Taylor-Papadimitriou, J. (1983) Complexity of expression of antigenic determinants recognised by monoclonal antibodies HMFG1 and HMFG2 in normal and malignant human epithelial cells. J. Immunol., 131, 508.

Critchley, M., McLaughlin, P. J., Brownless, S., Tromans, P. M. Patten, M. McDicken, I. W. (1986) Radionuclide localisation of epithelial ovarian tumours with $^{123}$I-labelled monoclonal antibody (H317). Clin. Radiol., 37, 107. and Johnson PM.

Daniels, M. R., Hancock, A. M., Walker, C. & Mates G. Interaction of vascular endothelial cells with normal and malignant cells. 3rd Int. Symp. on Biology of Vascular Endothelial Cells p. 57 MIT.

Easty, D. M., Easty, C. C., Carter, R. C., Monaghan, P. and Butler, C. J. (1981) Ten human carcinoma cell lines derived from squamous carcinomas of the head and neck. Br. J. Cancer, 43, 772.

Epenetos, A. A., Snook, B., Hooker G. and five others (1985) Indium-111 labelled moonoclonal antibody to PLAP in the detection of neoplasms of testis, ovary and cervix. Lancet ii, 350.

Fabricant, R. N., DeLarco, I. E. and Todaro, G. J. (1977) Nerve growth factor receptors on human melanoma cells in culture. Proc. Nat. Acad. Sci. USA., 74, 565.

Fogh, J. and Trempe, G. (1975) In New Human Tumour Cell Lines. Fogh, J. (Ed.), Human Tumour Cells In Vitro., pp115, Plenum Press: New York. Jacobs, J. P., Jones, C. M. and Baille, J. P. (1970) Characterisation of a human diploid cell line designated MRC-5. Nature, 227, 168.

Johnson, P. M. (1984) Immunobiology of the human trophoblast. In Immunological aspects of Reproduction in Mammals. Creighton, D. B. (ed.) p109, Butterworth Press: London.

Johnson, P. M., Cheng, H. M., Molloy, C. M., Stern, C. M. M. and Slade, M. B. (1981)Human trophoblast-specific surface antigens identified using monoclonal antibodies. Am. J. Reprod. Immunol., 1, 246.

Klein, E., Klein, G., Nadkarni, J. S., Nadkarni, J. J., Wigzell, H. and Clifford, P. (1967) Surface IgM specificity on cells derived from a Burkitts lymphoma. Lancet ii, 1068.

Kohler, G. and Milstein, C. (1975) Derivation of specific antibody-producing tissue culture and tumour cell lines by cell fusion. Eur. J. Immunol., 6, 511.

Krantz, M., Ariel, N. and Gold, P. (1979) CEA biology and chemistry: characterisation of partial proteolysis fragments. In: Carcino-embryonic proteins vol. 1. Lehmann, F.-G. (Ed.) p17, Elsevier/North Holland Biomedical Press: Amsterdam.

Kumar, S., West, D., Daniel, M., Hancock, A. and Carr, T. (1983) Human lung tumour cell lines adapted to grow in serum-free medium secretes angiogenesis factor. Int. J. Cancer, 32, 461.

Lipinski, M., Parks, D. R., Rouse, R. V., Herzenberg, L. A. (1981) Human trophoblast cell surface antigens defined by monoclonal antibodies. Proc. Natl. Acad. Sci. USA., 78, 5147.

Loke, Y. W and Day, S. (1984) Monoclonal antibody to human cytotrophoblast. Am. J. Reprod. Immunol., 5, 106.

Lowry, O. H., Rosebrough, N. T., Farr, A. L. and Randall, R. J. (1951) Protein measurement with the folin phenol reagent. J. Biol. Chem., 193, 265.

McDicken, I. W., McLaughlin, P. J., Tromans, P. M., Lenesley, D. M. and Johnson, P. M. (1985) Detection of placental-type alkaline phosphatase in ovarian cancer. Br. J. Cancer, 52, 59.

McLaughlin, P. J., Cheng, M. H., Slade, M. B. and Johnson, P. M. (1982) Expression on cultured human tumour cells of placental trophoblast membrane antigens and placental alkaline phosphatase defined by monoclonal antibodies. Int. J. Cancer., 30, 21.

McLaughlin, P. J. (1986) Cancer associated forms of human alkaline phosphatase. In Advances in Clinical Enzymology. Blaton, V. (Ed.) p30, S. Karger AG: Basel.

Minowada J., Ohnuma, T., and Moore, G. E. (1972) Rosette forming human lymphoid lines. J. Nat. Cancer. Inst., 49, 891.

Moore, A. E., Sabachewsky, L. and Toolen, H. W. (1955) Culture characteristics of four permanent lines of human cancer cells. Cancer Res., 15, 598.

Mueller, U. W., Hawes, C. S. and Jones, W. R. (1986) Cell surface antigens of human trophoblast: definition of an apparently unique system with a monoclonal antibody. Immunol., 59, 135.

O'Toole, C. M., Povey, S., Hepburn, P. and Franks, L. M. (1983). Identity of some human bladder cancer cell lines. Nature, 301, 429.

Patillo, R. A. and Gey, G. O. (1968) The establishment of human hormone-synthesizing cells in vitro. Cancer Res., 28, 1231.

Patillo, R. A., Ruckert, A., Hussa, R., Bernstein, R. and Delfs, E. (1971) The JAr cell line—continuous human multihormone production and controls. In Vitro, 6, 398.

Pateisky, N., Philipp, K., Skodler, W. D., Czerwenka, K., Hamilton, G. and Burchell, J. (1985). Radioimmunodetection in patients with suspected ovarian cancer. J. Nuc.Med, 26, 1369.

Plummer, T. H., Elder, J. H., Alexander, S., Phelan, A. W. and Tarentino, A. L. (1984). Demonstration of peptide: N-glycosidase F activity in endo-p-N-acetylglucosaminidase F preparations. J. Biol. Chem., 259, 10700.

Pulvertaft, R. J. V. (1964) Cytology of Burkitt's tumour (African lymphoma). Lancet i, 238.

Rettig, W. J., Cordon-Cardo, C., Koulos, J. P., Lewis, J. L., Oettgen, H. F. and Old, L. L. (1985) Cell surface antigens of human trophoblast and choriocarcinoma defined by monoclonal antibodies. Int. J. Cancer, 35, 469.

Ruoslahti, E. and Engvall, E. (1978) Alpha feto-protein. Scand. J. Immunol., 7 Suppl. 6, 1.

Smith, N. C., Brush, M. G. and Luckett, S. (1974) Preparation of human placental villous surface membrane. Nature, 252, 302.

Stern, P. L., Gilbert, P., Sternberg, S., Thompson, S. and Chada, K. (1984). A monoclonal antibody which detects 125 kDa glycoprotein on embryonal carcinoma cells and is mitogenic for murine spleen cells. J. Reprod. Immunol., 6, 313.

Stern, P. L., Berisford, N., Thompson, S., Johnson, P. M., Webb, P. D. and Hole, N. (1986).Characterisation of the human trophoblast leukocyte antigenic molecules defined by a monoclonal antibody. J. Immunol, 137, 1604.

Sunderland, C. A., Redman, C. W. G. and Stirrat, G. M. (1981) Monoclonal antibodies to human syncytiotrophoblast. Immunol., 43, 541.

Swallow, D. M., Gendler, S., Griffiths, By Corney, G., Taylor-Papadimitriou, J. and Bramwell, M. E. (1987) The human tumour-associated epithelial mucins are coded by and expressed hypervariable gene locus PUM. Nature, 328, 82.

Taylor-Papadimitriou J., Petersen, J. A., Arklie, J., Burchell, J., Ceriani,. R. L. and Bodmer, W. F. (1981) Monoclonal antibodies to epithelium specicifc component of the milk fat globule membrane: production and reaction with cells in culture. Int. J. Cancer, 28, 17.

Thompson, S., Stern, P. L., Webb, M. and six others (1984). Differentiation of neuron-like cells and other cell types from cloned human teratocarcinoma cells cultured in retinoic acid. J. Cell. Sci., 72, 37.

Travers, P. and Bodmer, W. (1984) Preparation and characterisation of monoclonal antibodies against placental alkaline phosphatase and other human trophoblast associated determinants. Int. J. Cancer. 33, 633.

Trowbridge, I. S., Newman, R. A., Domingo, D. L. and Sauvage, C. (1984).Transferrin receptor: structure and function. Biochem. Pharmacol., 33, 925.

Ullrich, A., Boll, J. R., Rhen, E. Y. and eleven others (1985) Human insulin receptor and its relationship to the tyrosine kinase family of oncogenes. Nature, 313, 756.

Walker, C., Daniels, M., and Mates, G. (1984) Proliferative response of human venous endothelial cells to medium conditioned by human tumour cells. Cell. Biol. Int. Rep., 8, 731.

Warr, B. G. and Cruickshank, D. J. (1987) Circulating tumour associated antigen detected by the monoclonal antibody HMFG2 in human epithelial ovarian cancer. Int. J. Cancer, 39, 30.

Waterfield, M. D., Mayes, E. L. V., Stroobant, P. and five others (1982). A monoclonal antibody to the human epidermal growth factor receptor. J. Cell. Biochem., 20, 149.

Webb, P. D., Evans, P. W., Molloy, C. M. and Johnson, P. M. (1985) Biochemical studies of human microvillous plasma membrane proteins. Am. J. Reprod. Immunol. Microbiol., 8, 113.

Wilkinson, M. J. S., Howell, A., Harris, M., Pad, J. T., Swindell, R. and Sellwood, R. A. (1984) The prognostic significance of two epithelial membrane antigens expressed by human mammary carcinoma. Int. J. Cancer, 33, 299.

Wiseman, G., Bramwell, M. E., Bhavanandan, V. P. and Harris, H. (1984).The structure of the Ca-antigen. Biochem. Soc. Trans., 12, 537.

Yamashita, K., Nakamura, T., Shimizu, T. and Ohno, H. (1986). Monoclonal antibodies to choriocarcinoma. Am. J.Reprod. Immunol. Microbiol., 11, 130.

Zeuthen, J., Nogaard, J. O. R., Avner, P. and five others (1980) Characterisation of an ovarian teratocarcinoma cell line. Int. J. Cancer, 25, 19.

What is claimed is:

1. A 5T4 antigen which is a glycoprotein characterized by the following properties:
  a. molecular weight of 72 KDa when subjected to SDS-polyacrylamide gel electrophoresis (PAGE) under reduced conditions and 69 KDa under non-reducing conditions;
  b. monomeric structure in the plasma membrane when subjected to gel filtration and two-dimensional SDS-PAGE-IEF (iso-electric focusing) and an isoelectric point of about 6.9;
  c. when subjected to N-linked sugar removal with N-glycanase has a 42 KDa core structure;
  d. native glycoprotein is N-terminus blocked and resistant when subjected to digestion with V8 protease, pepsin, chymotrypsin or chemical cleavage with 75% formic acid, hydroxylamine or N-chloro-succinimide;
  e. when subjected to high sensitivity amino acid analysis comprises most abundant residues as approximately 10% glutamic acid, 12% serine, 16% glycine, 9% threonine and 15% alanine;

f. N-linked carbohydrate structures that are not susceptible when subjected to endo beta-galactosidase digestion;

g. when subjected to N-linked sugar removal, the core structure is susceptible to Cleveland peptide mapping yielding major characteristic peptides of 16.5, 14.0 and 10 KDa with chymotrypsin digestion and 22, 13.5 and 11 KDa with V8 protease digestion;

h. when boiled and reduced native 5T4 antigen is also susceptible to V8 protease yielding major glycoproteins of 24, 12.5 and 10 KDa by Cleveland mapping;

i. 5T4 antigen when purified by reverse phase chromatography shows an unusually high ratio 280:215 nm absorption; and j said 5T4 antigen free of other human trophoblast cell membrane proteins.

2. A proteolytic fragment of 5T4 antigen capable of forming a complex with antibodies to 5T4 antigen.

3. The 42 KDa polypeptide core of 5T4 antigen and fragments of the 42 KDa core capable of forming a complex with antibodies to 5T4 antigen.

4. A process for the production of 5T4 antigen free of other human trophoblast cell membrane proteins which comprises:

(a) recovering the syncytiotrophoblast glycoproteins from human placenta by solubilizing in buffers;

(b) subjecting these glycoproteins to purification by at least one of antibody affinity chromatography, hydrophobic interaction reverse phase chromatographic methods or gel filtration;

(c) isolating 5T4 antigen, and (d) recovering 5T4 antigen free of other human trophoblast cell membrane proteins.

5. An antigen according to claim 1 bearing a detectable label.

6. An antigen according to claim 1 immobilised on a solid support.

7. An antigen according to claim 2 bearing a detectable label.

8. An antigen according to claim 2 immobilized on a solid support.

9. A composition comprising an antigen according to claim 2 together with a pharmaceutically acceptable diluent or carrier.

10. An antigen or fragment thereof according to claim 3 bearing a detectable label.

11. An antigen or fragment thereof according to claim 3 immobilized on a solid support.

12. A composition comprising an antigen according to claim 3 together with a pharmaceutically acceptable diluent or carrier.

13. A composition comprising an antigen or fragment thereof according to claim 1 bearing a detectable label together with an acceptable diluent or carrier.

* * * * *